United States Patent
Enoki

(10) Patent No.: US 11,135,020 B2
(45) Date of Patent: Oct. 5, 2021

(54) IMAGE PROCESSING DEVICE AND METHOD, SURGICAL SYSTEM, AND SURGICAL MEMBER

(71) Applicant: SONY CORPORATION, Tokyo (JP)

(72) Inventor: Junichiro Enoki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 347 days.

(21) Appl. No.: 16/075,018

(22) PCT Filed: Mar. 16, 2017

(86) PCT No.: PCT/JP2017/010579
§ 371 (c)(1),
(2) Date: Aug. 2, 2018

(87) PCT Pub. No.: WO2017/169823
PCT Pub. Date: Oct. 5, 2017

(65) Prior Publication Data
US 2019/0038364 A1    Feb. 7, 2019

(30) Foreign Application Priority Data
Mar. 30, 2016 (JP) .............................. JP2016-067416

(51) Int. Cl.
*A61B 34/20* (2016.01)
*A61F 9/007* (2006.01)
(Continued)

(52) U.S. Cl.
CPC ............... *A61B 34/20* (2016.02); *A61B 1/00* (2013.01); *A61B 1/313* (2013.01); *A61B 3/13* (2013.01);
(Continued)

(58) Field of Classification Search
CPC .. A61B 1/00; A61B 34/20; A61B 3/13; A61B 9/20; A61F 9/007
See application file for complete search history.

(56) References Cited

U.S. PATENT DOCUMENTS 9,597,009 B2    3/2017 Ren et al.
2002/0188172 A1*  12/2002 Irion ...................... A61B 1/04
600/117
(Continued)

FOREIGN PATENT DOCUMENTS

| JP | 10-328126 A | 12/1998 |
|---|---|---|
| JP | 2005-304633 A | 11/2005 |

(Continued)

OTHER PUBLICATIONS

"Unified Detection and Tracking in Retinal Microsurgery" by R. Sznitman et al. MICCAI. Part I, LNCS 6891, pp. 1-8. (Year: 2011).*

(Continued)

*Primary Examiner* — Jason M Ip
(74) *Attorney, Agent, or Firm* — Xsensus LLP

(57) ABSTRACT

The present invention relates to an image processing device and method, a surgical system, and a surgical member with which a position and an orientation of the surgical member for surgery of a subject can be easily grasped. The present invention acquires a microscopic image (201) obtained by photographing the surgical member (121) inserted to the subject with a surgical microscope (112), estimates the relative posture of the surgical member in the subject on the basis of the acquired microscopic image (201), and outputs posture information (222, 223, 224) associated with the posture that has been estimated. The present invention can be applied to ophthalmic surgery, in which an intraocular endoscope or surgical tool is observed with a surgical microscope, for example.

5 Claims, 13 Drawing Sheets

(51) Int. Cl.
  *A61B 1/00* (2006.01)
  *A61B 3/13* (2006.01)
  *A61B 90/20* (2016.01)
  *A61B 1/313* (2006.01)

(52) U.S. Cl.
  CPC .............. *A61B 90/20* (2016.02); *A61F 9/007* (2013.01); *A61B 2034/2057* (2016.02)

(56) References Cited

U.S. PATENT DOCUMENTS

2010/0168763 A1  7/2010  Zhao et al.
2015/0173644 A1  6/2015  Ren et al.

FOREIGN PATENT DOCUMENTS

JP   2014-155592 A   8/2014
JP      2015-2858 A   1/2015

OTHER PUBLICATIONS

"Parametric Eyeball Model for Interactive Simulation of Ophthalmologic Surgery" by Y. Cai et al. MICCAI 2001, LNCS 2208, pp. 465-472 (Year: 2001).*
International Search Report dated May 30, 2017 in PCT/JP2017/010579, citing documents AA and AO therein, 3 pages.
Office Action dated Jan. 12, 2021 in Japanese Patent Application No. 2018-509008, 4 pages.

* cited by examiner

IMAGE PROCESSING DEVICE AND METHOD, SURGICAL SYSTEM, AND SURGICAL MEMBER

TECHNICAL FIELD

The present technology relates to an image processing device and method, a surgical system, and a surgical member, and in particular, to an image processing device and method, a surgical system, and a surgical member with which a position and an orientation of the surgical member for surgery of an eye can be easily grasped.

BACKGROUND ART

In ophthalmic surgery, sometimes, an intraocular endoscope is used in a case of treating a position that cannot be visually recognized from a microscope. An intraocular endoscope is often used especially for retinal vitreous surgery and the like.

FIG. 1 is a diagram for explaining surgery of an eye. An intraocular endoscope 11 and a surgical tool 12 are inserted to a subject eye 21. An image 41 of an inside of the subject eye 21 photographed by the intraocular endoscope 11 is displayed on a monitor 31. A surgeon performs surgery while seeing the image 41 of the monitor 31. Although the intraocular endoscope 11 has a high degree of freedom of a photographing position, there is a problem that the gravity direction and a position in the image are easily lost. Furthermore, if wrongly operated, the intraocular endoscope 11 may damage a retina 13.

Therefore, the hurdle for learning the operation of the intraocular endoscope 11 is very high. Furthermore, in the current course, guidance is given to return to a home position in a case where the position is lost, so the surgery time will be longer. Accordingly, it is required that an orientation and a position of the intraocular endoscope 11 are easily grasped.

Therefore, it has been proposed to provide an index pointing a specific direction at the hand portion of an ophthalmic endoscope (Patent Document 1). Further, it is proposed to use a gravity sensor or an acceleration sensor to obtain a direction of an endoscope (Patent Document 2). Furthermore, it has been proposed to detect a marker with an X-ray of an endoscope for observing the duodenum from an X-ray image (Patent Document 3).

CITATION LIST

Patent Document

Patent Document 1: Japanese Patent Application Laid-Open No. 10-328126
Patent Document 2: Japanese Patent Application Laid-Open No. 2014-155592
Patent Document 3: Japanese Patent Application Laid-Open No. 2015-2858

SUMMARY OF THE INVENTION

Problems to be Solved by the Invention

However, in the proposal of Patent Document 1, it is necessary for an operator to visually recognize fundamentals of the ophthalmic endoscope or to confirm the index with the feel of a fingertip. In the former case, the line of sight gets away from a surgical field. In the latter case, there is a problem that it is necessary to become accustomed to grasping the correct orientation. Furthermore, it is difficult to grasp the position. In addition, ophthalmic endoscopes are becoming thinner due to minimally invasive procedures, and despite the fact that distortion is likely to occur, it is difficult to cope with a case where distortion occurs between a root and a tip end.

Attaching a sensor to a tip end portion of an endoscope as proposed in Patent Document 2 becomes an obstacle to thinning the diameter. Furthermore, although it is somewhat useful to attach a sensor to a hand portion, the weight of the endoscope itself is increased, operation becomes difficult, and application to an intraocular endoscope is difficult.

As in the proposal of Patent Document 3, in order to utilize an X-ray image, not only an X-ray device is necessary but also an endoscope itself for observing the duodenum needs to have a special structure, and the device becomes large in scale, resulting in high cost. Accordingly, it is difficult to apply to an endoscope.

The present technology has been made in view of such a situation, and is to enable a position and an orientation of a surgical member for surgery of an eye to be easily grasped.

Solutions to Problems

One aspect of the present technology is an image processing device including: an acquisition unit that acquires a microscopic image obtained by photographing a surgical member inserted to a subject with a surgical microscope; an estimation unit that estimates a relative posture of the surgical member in the subject on the basis of the microscopic image acquired by the acquisition unit; and an output unit that outputs posture information associated with the posture that has been estimated.

The surgical member may be an intraocular endoscope.

The output unit can superimpose the posture information on an endoscopic image output by the intraocular endoscope and output the superimposed image.

The posture can include at least one of a position, an orientation, and a rotation angle.

The posture information can include a graphic representing a position, an orientation, and a rotation angle on a scale.

The posture information can include a cross-sectional or three-dimensional view of an eyeball model.

A marker is displayed on the surgical member, and the estimation unit estimates the relative posture of the surgical member in the subject on the basis of the marker of the microscopic image acquired by the acquisition unit.

The acquisition unit acquires an image of the intraocular endoscope photographed from the outside of a subject eye as the subject, and the estimation unit can estimate the relative posture of the intraocular endoscope in the subject eye on the basis of a feature amount of a portion not inserted to the subject eye of the intraocular endoscope.

The surgical member is a surgical tool on which a marker is displayed, the acquisition unit can acquire the microscopic image of the surgical tool on which the marker is displayed and an endoscopic image of a intraocular endoscope, the estimation unit can estimate a relative posture between the surgical tool on which the marker is displayed and the surgical microscope, and also estimate a relative posture between the surgical tool on which the marker is displayed and the intraocular endoscope, and the image processing device further includes an operation unit that operates a relative posture between the surgical microscope and the intraocular endoscope from the relative posture between the surgical tool and the surgical microscope and the relative posture between the surgical tool and the intraocular endoscope.

One aspect of the present technology is an image processing method including: a step of acquiring a microscopic image obtained by photographing a surgical member inserted to a subject with a surgical microscope; a step of estimating a relative posture of the surgical member in the subject on the basis of the microscopic image acquired by the acquisition unit; and a step of outputting posture information associated with the posture that has been estimated.

One aspect of the present technology is a surgical system including: a surgical microscope that photographs a subject; an acquisition unit that acquires a microscopic image obtained by photographing a surgical member inserted to a subject with a surgical microscope; an estimation unit that estimates a relative posture of the surgical member in the subject on the basis of the microscopic image acquired by the acquisition unit; and an output unit that outputs posture information associated with the posture that has been estimated.

One aspect of the present technology is a surgical member that is inserted to a subject eye of a subject person and is used for surgery of the subject eye, and is a surgical member in which a marker that can be observed by a surgical microscope is displayed in an insertion unit to be inserted to the subject eye.

In one aspect of the present technology, a microscopic image obtained by photographing a surgical member inserted to a subject with a surgical microscope is acquired, a relative posture of the surgical member in the subject is estimated on the basis of the acquired microscopic image, and posture information associated with the posture that has been estimated is output.

Effects of the Invention

As described above, according to one aspect of the present technology, a position and an orientation of a surgical member for surgery of an eye can be easily grasped.

Note that the effects described herein are merely illustrative, and are not limitative, and the present technology may have additional effects.

MODE FOR CARRYING OUT THE INVENTION

Hereinafter, a mode for implementing the present technology (hereinafter referred to as an embodiment) will be described. Note that the description will be made in the following order.

Figure 1:
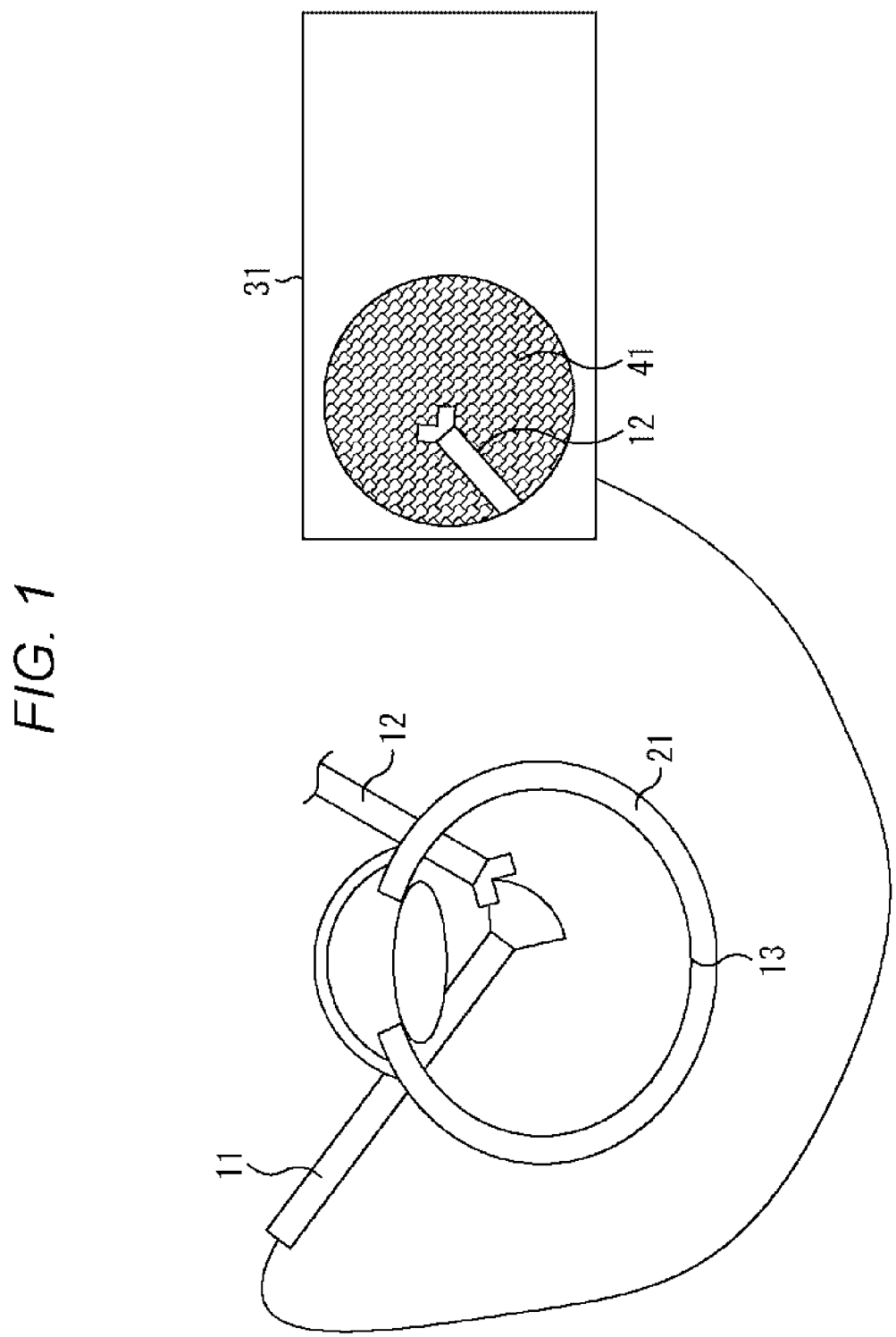
FIG. 1 is a diagram for explaining eye surgery.
Figure 2:
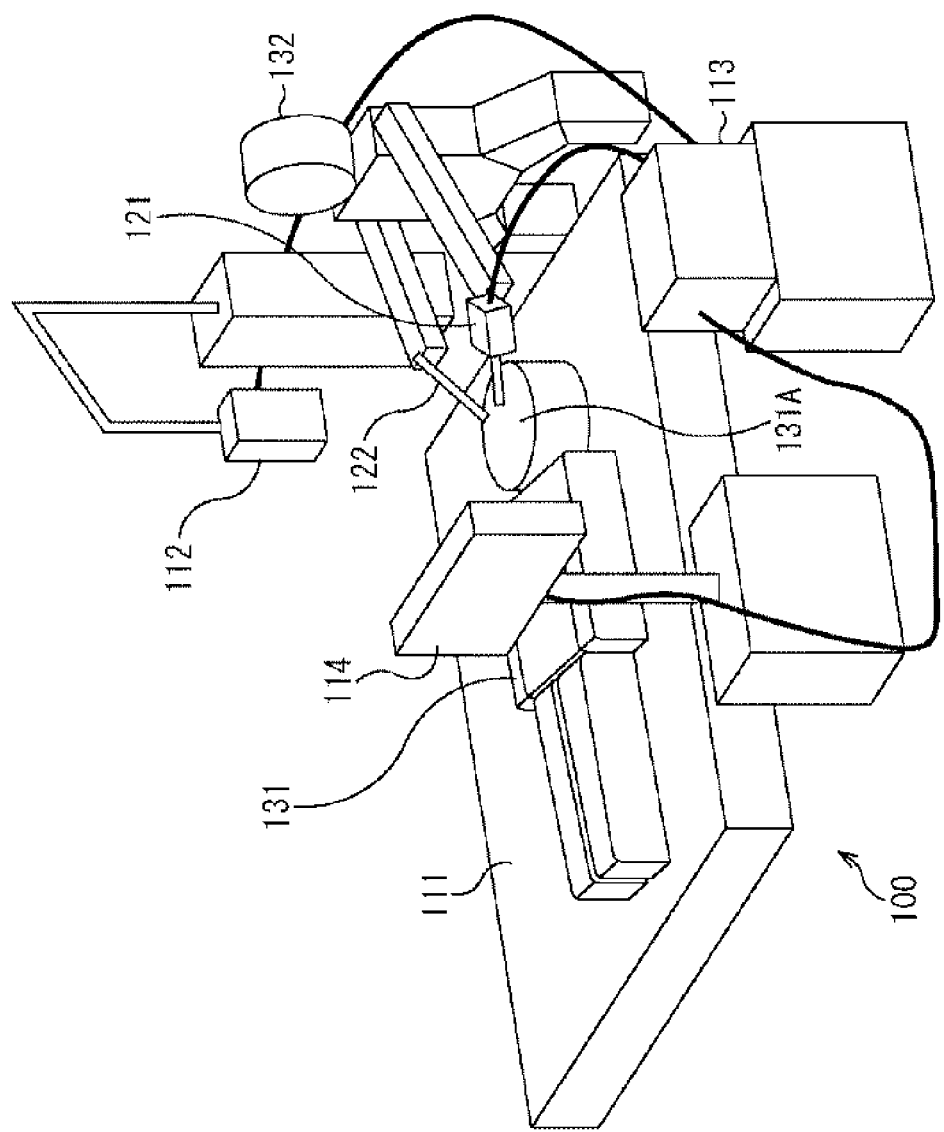
FIG. 2 is a perspective view showing a configuration of a surgical system according to an embodiment of the present technology.

1. First Embodiment
(1) Surgical system
(2) Principle of posture estimation
(3) Functional block of surgical system
(4) Image processing
2. Second Embodiment
3. Third Embodiment
(1) Principle of posture estimation
(2) Functional block of surgical system
(3) Image processing
4. Posture Information
5. Other 1. First Embodiment (1) Surgical System FIG. 2 is a perspective view showing a configuration of a surgical system according to an embodiment of the present technology. FIG. 2 schematically shows a basic configuration of a surgical system 100 for ophthalmic surgery. The surgical system 100 includes a surgical table 111, a surgical microscope 112, an image processing device 113, and a presentation unit 114. In addition, a vitreous body surgical device, a vital display device, or the like can be used as necessary, but illustration thereof is omitted.

A subject person (that is, a patient) 131 is laid on the surgical table 111. A surgeon 132 stands on a rear side (or may be a left side or a right side) of a head portion 131A of the subject person 131, and performs ophthalmic surgery using an ophthalmic surgical member. In a case of the example shown in FIG. 2, an intraocular endoscope 121, and a surgical tool 122 such as, for example, a vitreous body cutter are used as surgical members.

A surgical microscope 112 is arranged above the head portion 131A of the subject person 131, and photographs a subject eye 151 (see FIG. 3 as described later) of the subject person 131 as a subject. In a case where the intraocular endoscope 121 and the surgical tool 122 are inserted to the subject eye 151, the subject eye 151 in a state where the intraocular endoscope 121 and the surgical tool 122 are inserted is photographed.

An image signal photographed by the surgical microscope 112 is supplied to the image processing device 113. When inserted to the subject eye 151, the intraocular endoscope 121 photographs an internal state of the subject eye 151, and outputs the image signal thereof to the image processing device 113. The image processing device 113 outputs the image corresponding to the input image signal to the presentation unit 114. With this configuration, the surgeon 132 can see the image photographed by the surgical microscope 112 (hereinafter referred to as a microscopic image) and the image photographed by the intraocular endoscope 121 (hereinafter referred to as an endoscopic image) during the surgery. Note that, sometimes, a monitor is attached to the surgical microscope 112, and the image on the monitor can be seen.

A position of the surgical microscope 112 can be arbitrarily changed. Furthermore, a posture of the intraocular endoscope 121 can be changed by operation by the surgeon 132. With this configuration, an arbitrary portion of the subject eye 151 can be observed.

(2) Principle of Posture Estimation

Figure 3:
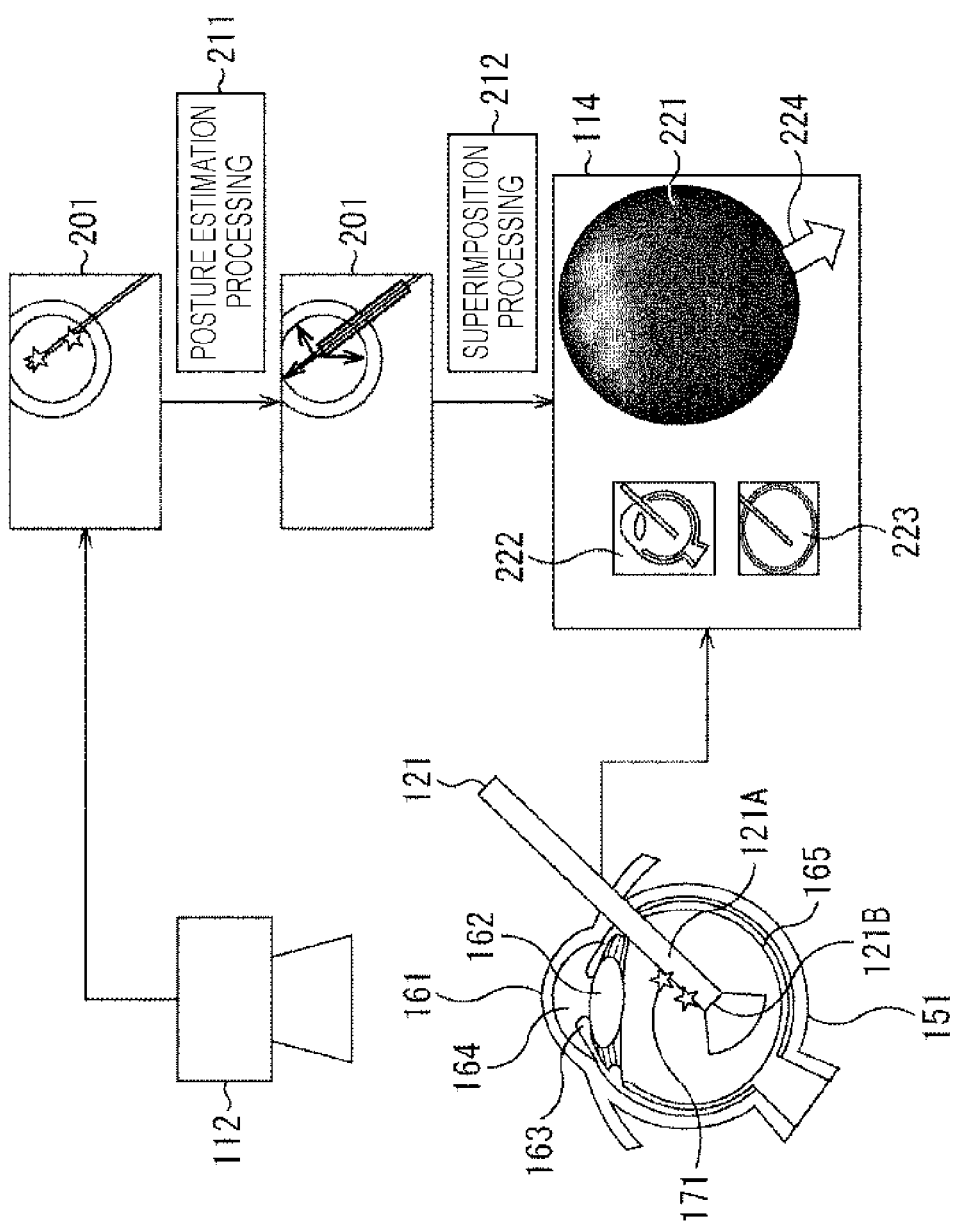
FIG. 3 is a diagram for explaining eye surgery according to an embodiment of the present technology.

FIG. 3 is a diagram for explaining eye surgery according to an embodiment of the present technology. Hereinafter, the principle of posture estimation of the intraocular endoscope 121 will be described with reference to FIG. 3.

FIG. 3 shows a cross-sectional configuration of the subject eye 151 of the subject person 131. An upper part of the subject eye 151 is covered with a cornea 161. A crystalline lens 162 exists further behind an anterior chamber 164 under the cornea 161, and an iris 163 exists on the left and right thereof. Furthermore, a retina 165 exists behind the spherical subject eye 151.

An insertion unit 121A of the intraocular endoscope 121 is inserted to the subject eye 151, and a photographed portion is illuminated with illumination light from a tip end 121B, and the internal state is photographed. A marker 171 for confirming the posture of the intraocular endoscope 121 is displayed on the insertion unit 121A. This marker 171 can be confirmed with a microscopic image photographed by the surgical microscope 112.

Figure 4:
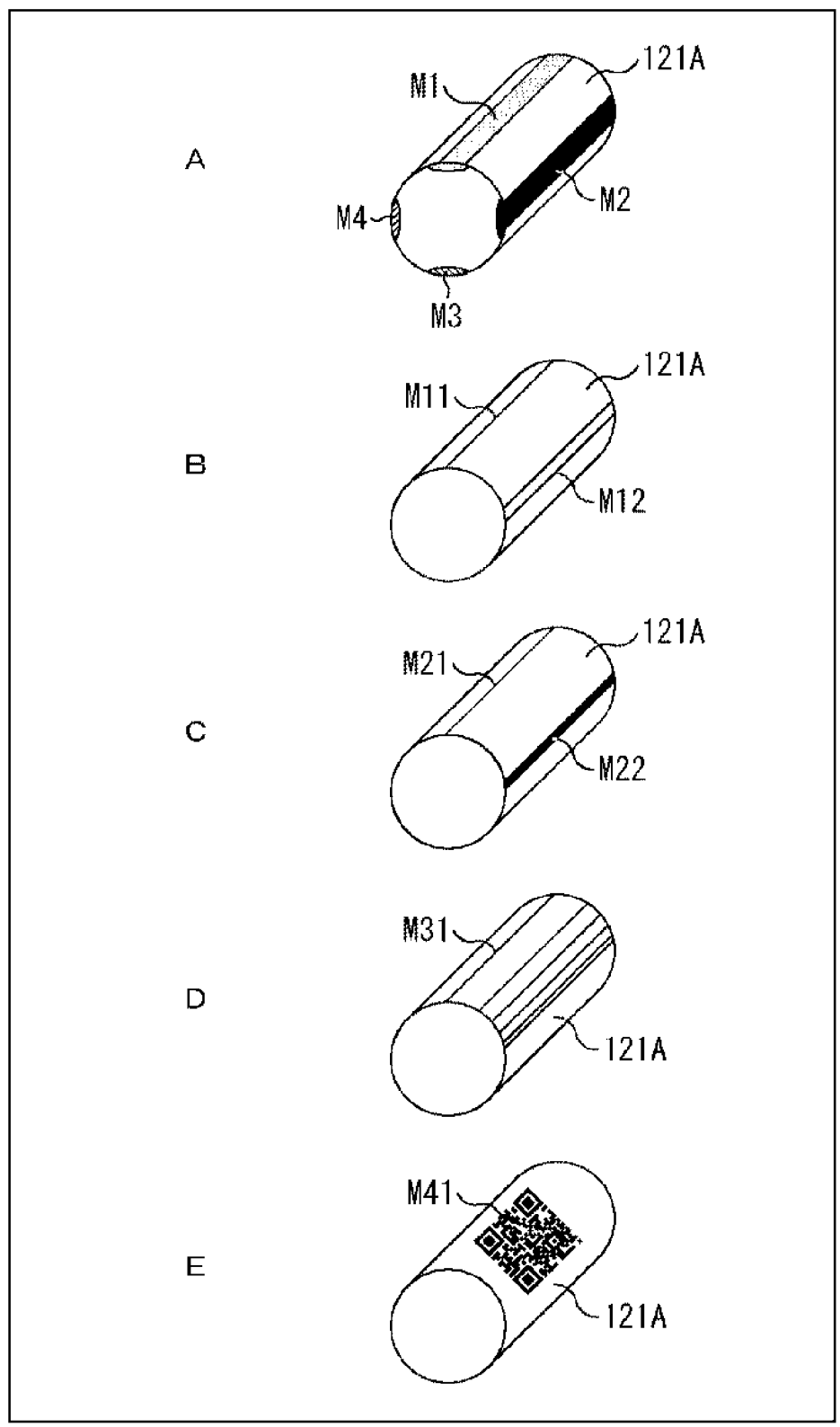
FIG. 4 is a diagram for explaining a marker of the present technology.

A specific example of the marker 171 will now be described with reference to FIG. 4. FIG. 4 is a diagram for explaining a marker of the present technology. Note that a marker Mx (x is a number) in FIG. 4 corresponds to the marker 171 in FIG. 3.

In A of FIG. 4, bands of red, blue, green, and yellow are displayed along a length direction of the insertion unit 121A, on the outer surface of the insertion unit 121A of the intraocular endoscope 121 so that the bands can be observed with a microscopic image of the surgical microscope 112. For example, a red band M1 is displayed on the upper side of the intraocular endoscope 121, and a blue band M2 is displayed at a position rotated counterclockwise by 90 degrees from the red band M1. Moreover, a green band M3 is displayed at a position rotated counterclockwise by 180 degrees from the red band M1, and a yellow band M4 is displayed at a position rotated counterclockwise by 270 degrees from the red band M1.

Accordingly, a rotation angle of the intraocular endoscope 121 can be estimated from the microscopic image obtained by imaging the intraocular endoscope 121 of which the insertion unit 121A is inserted to the subject eye 151, with the surgical microscope 112. For example, in a case where the red band M1 is observed, it can be seen that the intraocular endoscope 121 is located at a reference position (a position at which the red band M1 is arranged on an upper side), that is, the rotation angle is 0 degree. In a case where the blue band M2 is observed, it can be seen that the intraocular endoscope 121 is rotated counterclockwise by 90 degrees from the reference position.

Hereinafter, similarly, in a case where the green band M3 is observed, it can be seen that the rotation angle from the reference position of the intraocular endoscope 121 is 180 degrees. In a case where the yellow band M4 is observed, it can be seen that the rotation angle from the reference position of the intraocular endoscope 121 is 270 degrees. In a case where the red band M1 and the blue band M2 are observed, it can be seen that the rotation angle from the reference position of the intraocular endoscope 121 is 45 degrees.

B of FIG. 4 represents an example in which different numbers of lines are displayed at predetermined positions as markers. In this example, the number of lines of a marker M11 at the reference position is one, and the number of lines of the marker M12 at the position rotated counterclockwise by 90 degrees from the reference position is two. Likewise, although not illustrated, the number is three at the position rotated counterclockwise by 180 degrees from the reference position, and four at the position rotated counterclockwise by 270 degrees. Also in this example, the rotation angle of the intraocular endoscope 121 can be estimated from the observed state of the marker.

C of FIG. 4 shows an example of markers having different line thicknesses. A line of a marker M21 at the reference position is the thinnest, and a thickness of a line of a marker M22 at the position rotated counterclockwise by 90 degrees from the reference position is thicker than the marker M21. Likewise, although not illustrated, a line of a marker at a position rotated counterclockwise by 180 degrees from the reference position is thicker than the marker M22, and a line of a marker at a position rotated counterclockwise by 270 degrees is further thicker than the marker at the position of 180 degrees. Also in this example, the rotation angle of the intraocular endoscope 121 can be estimated from the observed state of the marker.

D of FIG. 4 represents an example of a marker whose line interval varies depending on position. In other words, in this example, lines with different intervals in accordance with the rotation angle from the reference position of the intraocular endoscope 121 are displayed as a marker M31. Also in this example, the rotation angle of the intraocular endoscope 121 can be estimated from the observed state of the marker.

E of FIG. 4 shows an example of a marker of a specific pattern. In this example, a two-dimensional barcode is displayed on the insertion unit 121A, as the marker 41. Also in this example, the rotation angle of the intraocular endoscope 121 can be estimated from the observed state of the marker.

With reference to FIG. 3 again, a microscopic image 201 is obtained by photographing the subject eye 151 with the surgical microscope 112. A marker 171 (Mx) projected on the microscopic image 201 can be analyzed so that posture estimation processing 211 for estimating the posture of the intraocular endoscope 121 can be performed. Next, a superimposition processing 212 is performed to superimpose the posture that has been estimated on the image of the intraocular endoscope 121.

An endoscopic image 221 photographed by the intraocular endoscope 121 and graphic images 222, 223, and 224 representing the posture that has been estimated of the intraocular endoscope 121 are displayed on the presentation unit 114. Details of the graphic images 222, 223, and 224 representing postures will be described later as posture information with reference to FIGS. 11 to 14. Here, graphic images 222 and 223 representing the posture of the intraocular endoscope 121 and a graphic image 224 of an arrow indicating the gravity direction are displayed in a graphic of the sectional shape of the subject eye 151.

(3) Functional Block of Surgical System

Figure 5:
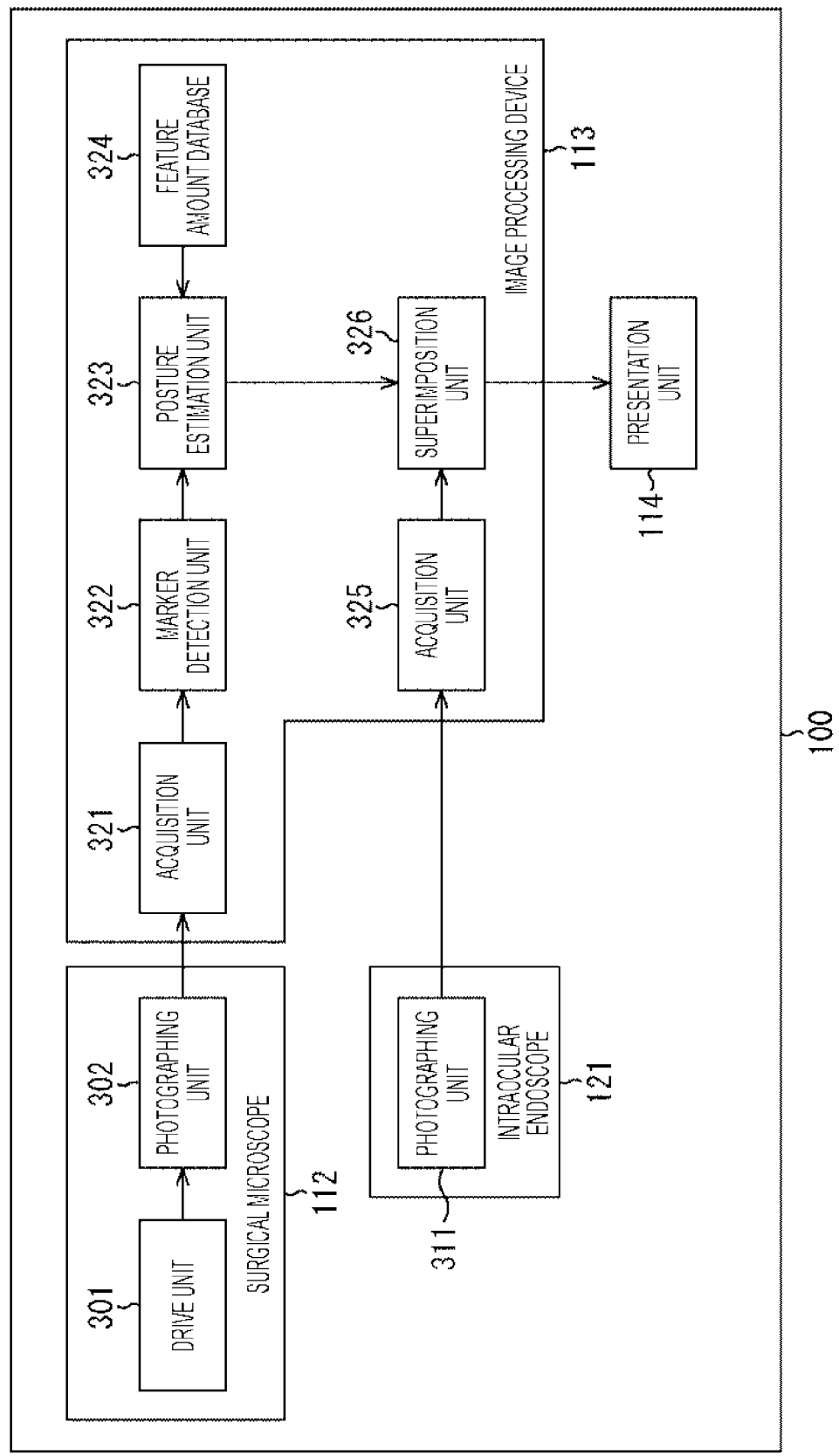
FIG. 5 is a block diagram showing a functional configuration of a surgical system of the present technology.

FIG. 5 is a block diagram showing a functional configuration of a surgical system of the present technology. As shown in FIG. 5, the surgical microscope 112 of the surgical system 100 has a drive unit 301 and a photographing unit 302. The photographing unit 302 includes a camera and an illumination unit, is moved to an arbitrary position with respect to the subject eye 151 by the drive unit 301, and performs photographing from that position.

The intraocular endoscope 121 has a photographing unit 311 including a camera and an illumination unit. The internal state of the intraocular endoscope 121 can be photographed by the photographing unit 311.

The image processing device 113 has an acquisition unit 321, a marker detection unit 322, a posture estimation unit 323, a feature amount database 324, an acquisition unit 325, and a superimposition unit 326.

The acquisition unit 321 acquires an image signal of a microscopic image obtained by photographing by the photographing unit 302 of the surgical microscope 112. The marker detection unit 322 detects the marker 171 from the image signal acquired by the acquisition unit 321. The posture estimation unit 323 estimates the posture of the intraocular endoscope 121 from the photographing state of the marker 171 detected by the marker detection unit 322. The feature amount database 324 holds in advance image information necessary for the posture estimation unit 323 to estimate the posture of the intraocular endoscope 121 from the photographing state of the marker 171. The posture estimation unit 323 outputs an image corresponding to the posture that has been estimated.

Three-dimensional position information (feature points) of the intraocular endoscope 121 on which the marker 171 is displayed is stored in the feature amount database 324. In a case where a plurality of feature points of which three-dimensional positions are known exist in a two-dimensional image (that is, a microscopic image), the relative three-dimensional position and posture of the camera (photographing unit 302 of the surgical microscope 112) with respect to the feature points can be obtained by solving a perspective N point problem (PNPP). Accordingly, conversely, the three-dimensional position and posture of the feature point can be obtained with the position of the imaging unit 302 of the surgical microscope 112 as a reference, and the position and posture of the intraocular endoscope 121 can be obtained from the three-dimensional position and posture of the feature point. In other words, information necessary for solving the PNPP including parameters such as the angle of view and the amount of distortion of the imaging unit 302 is stored in advance in the feature amount database 324.

The acquisition unit 325 acquires the endoscopic image photographed by the photographing unit 311 of the intraocular endoscope 121. The superimposition unit 326 superimposes the image representing the posture from the posture estimation unit 323 and the endoscopic image of the intraocular endoscope 121 acquired by the acquisition unit 325, and outputs the superimposed image to the presentation unit 114 for presentation.

(4) Image Processing

Figure 6:
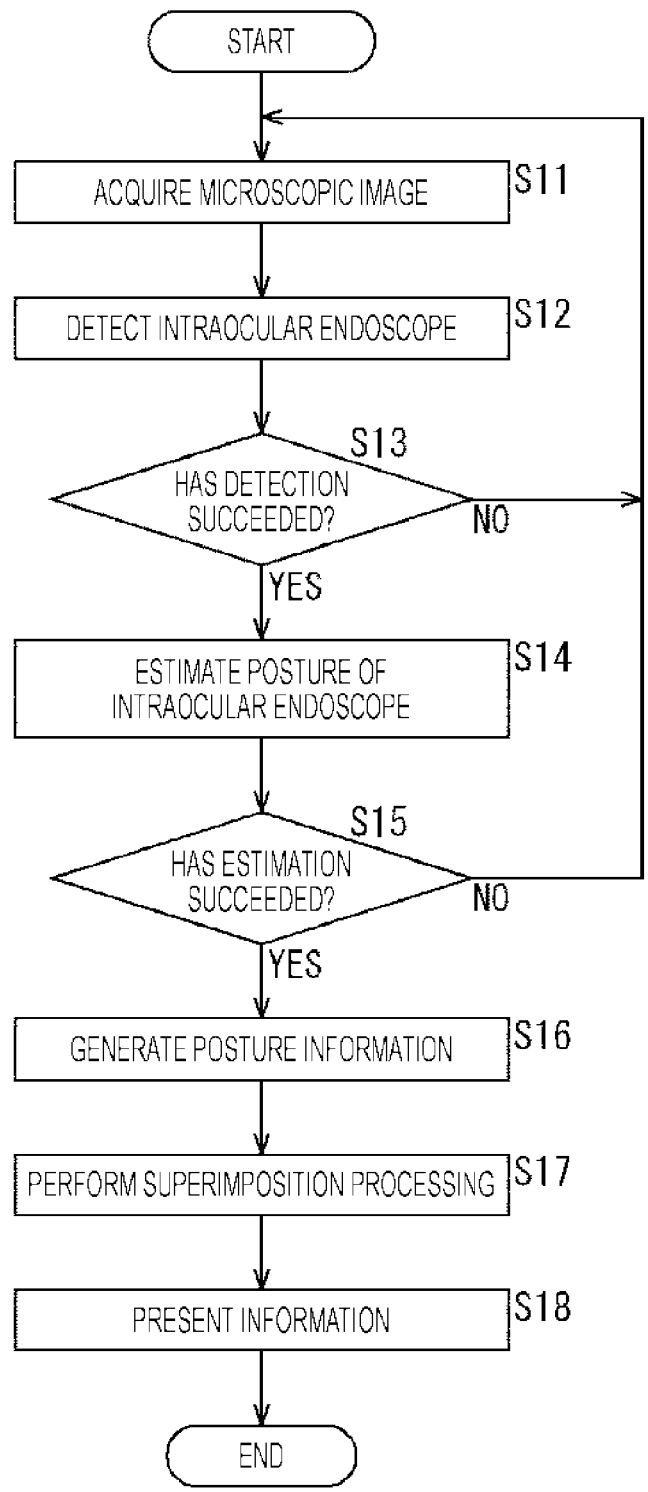
FIG. 6 is a flowchart for explaining image processing of the present technology.

Operation of the surgical system 100 of FIG. 5 will now be described with reference to FIG. 6. FIG. 6 is a flowchart for explaining image processing of the present technology.

In step S11, the acquisition unit 321 acquires the microscopic image. The image signal of the acquired microscopic image is supplied to the marker detection unit 322. That is, the subject eye 151 is photographed by the imaging unit 302 arranged at a predetermined position in advance by the drive unit 301 so that the entire subject eye 151 can be seen. As shown in FIG. 3, when the insertion unit 121A of the intraocular endoscope 121 is inserted to the subject eye 151, the marker 171 appears in the acquired microscopic image.

In step S12, the marker detection unit 322 detects the intraocular endoscope 121. In other words, the intraocular endoscope 121 is detected from the acquired microscopic image photographed by the photographing unit 302 of the surgical microscope 112. Note that detection accuracy can be improved by performing detection processing using past detection results. In step S13, the marker detection unit 322 determines whether detection is successful. In a case where the marker 171 cannot be detected yet, the processing returns to step S11. That is, the processing of detecting the marker 171 from the acquired microscopic image is repeated.

In a case where the detection of the marker 171 succeeds, the marker detection unit 322 supplies the detection result to the posture estimation unit 323. In step S14, the posture estimation unit 323 estimates the posture of the intraocular endoscope 121.

In other words, as described with reference to FIG. 4, the state of the marker 171 in the microscopic image obtained by photographing the intraocular endoscope 121 with the surgical microscope 112 varies depending on the posture of the intraocular endoscope 121. The image of the marker 171 corresponding to an arbitrary rotation angle is stored in the feature amount database 324, and the rotation angle of the intraocular endoscope 121 can be estimated by retrieving an image corresponding to the observed image of the marker 171 from the stored image of the marker 171.

Note that the posture of the intraocular endoscope 121 is specified by the position and orientation in addition to the rotation angle (rotation amount). The position and orientation can be estimated by solving the PNPP.

In step S15, the posture estimation unit 323 determines whether the estimation is successful. In a case where the posture of the intraocular endoscope 121 cannot be estimated yet, the processing returns to step S11, and the processing in step S11 and subsequent steps is repeated.

In a case where the posture of the intraocular endoscope 121 can be estimated, the posture estimation unit 323 generates posture information in step S16. In other words, posture information corresponding to the posture that has been estimated is generated. Details of this posture information will be described later with reference to FIGS. 11 to 14.

In step S17, the superimposition unit 326 performs superimposition processing. In other words, the superimposition unit 326 superimposes the image corresponding to the posture estimated by the posture estimation unit 323 on the endoscopic image photographed by the imaging unit 311 of the intraocular endoscope 121 acquired by the acquisition unit 325, and supplies the superimposed image to the presentation unit 114. In step S18, the presentation unit 114 presents information. In other words, an endoscopic image photographed by the intraocular endoscope 121 and an image corresponding to the posture estimated by the posture estimation unit 323 are presented on the presentation unit 114.

The surgeon 132 can confirm the posture of the endoscope 121 on the basis of the presented information. Accordingly, the surgeon 132 can operate the intraocular endoscope 121 as necessary, to confirm a desired portion, and operate the surgical tool 122, thereby performing surgery safely.

2. Second Embodiment

In the first embodiment, the marker 171 is displayed on the insertion unit 121A of the intraocular endoscope 121, and the marker 171 is observed, so that the posture of the intraocular endoscope 121 is estimated. In a second embodiment, the posture is estimated from the feature amount from the outside of the intraocular endoscope 121 without adding the marker 171. Hereinafter, the second embodiment will be described with reference to FIG. 7.

Figure 7:
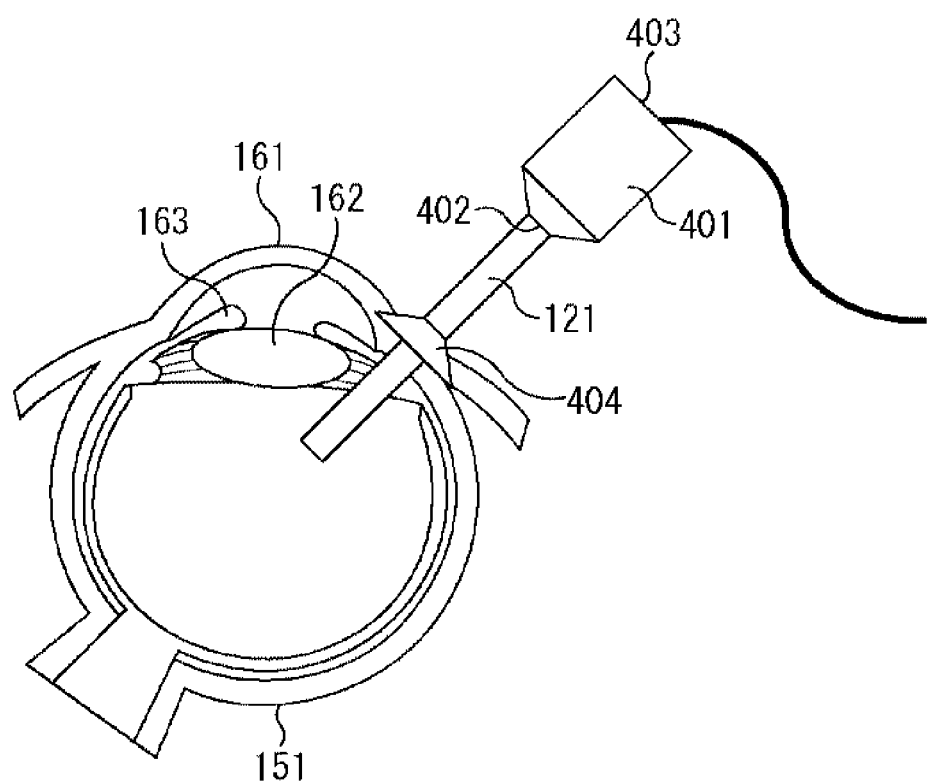
FIG. 7 is a diagram for explaining eye surgery according to an embodiment of the present technology.

FIG. 7 is a diagram for explaining eye surgery according to an embodiment of the present technology. FIG. 7 shows a state where the insertion unit 121A of the intraocular endoscope 121 is inserted from a trocar 404 to the subject eye 151. A thick handle 401 is attached to a side opposite to the thin insertion unit 121A of the intraocular endoscope 121 via a truncated conical bonding portion 402. The handle 401 is provided with an edge for preventing slippage and a cable 403 is connected thereto.

The configuration of the surgical system 100 according to the second embodiment is basically the same as that of the first embodiment. However, the angle of view is changed so that the wider range can be photographed, for example by arranging the surgical microscope 112 at a position away from the subject eye 151 than in the case of the first embodiment. Alternatively, a wide-angle lens can be used. Then, a member (hereinafter referred to as an external member) located outside the subject eye 151 other than the insertion unit 121A such as the handle 401, the bonding portion 402, the cable 403, the trocar 404, or the like is photographed and the feature amount of the external member is detected and learned from the photographed image. Of course, an imaging unit separate from the surgical microscope 112 may be provided so as to detect the feature amount of the external member. Accordingly, in the case of the second embodiment, the feature amount database 324 stores the feature amount necessary for estimating the purification of the intraocular endoscope 121 from the feature amount of the external member.

Since the operation of the second embodiment is similar to that of the first embodiment, description thereof is omitted. In the case of the second embodiment, since there is no need to display the marker 171 on the intraocular endoscope 121, the number of kinds of intraocular endoscopes 121 that can be used increases.

3. Third Embodiment

Figure 8:
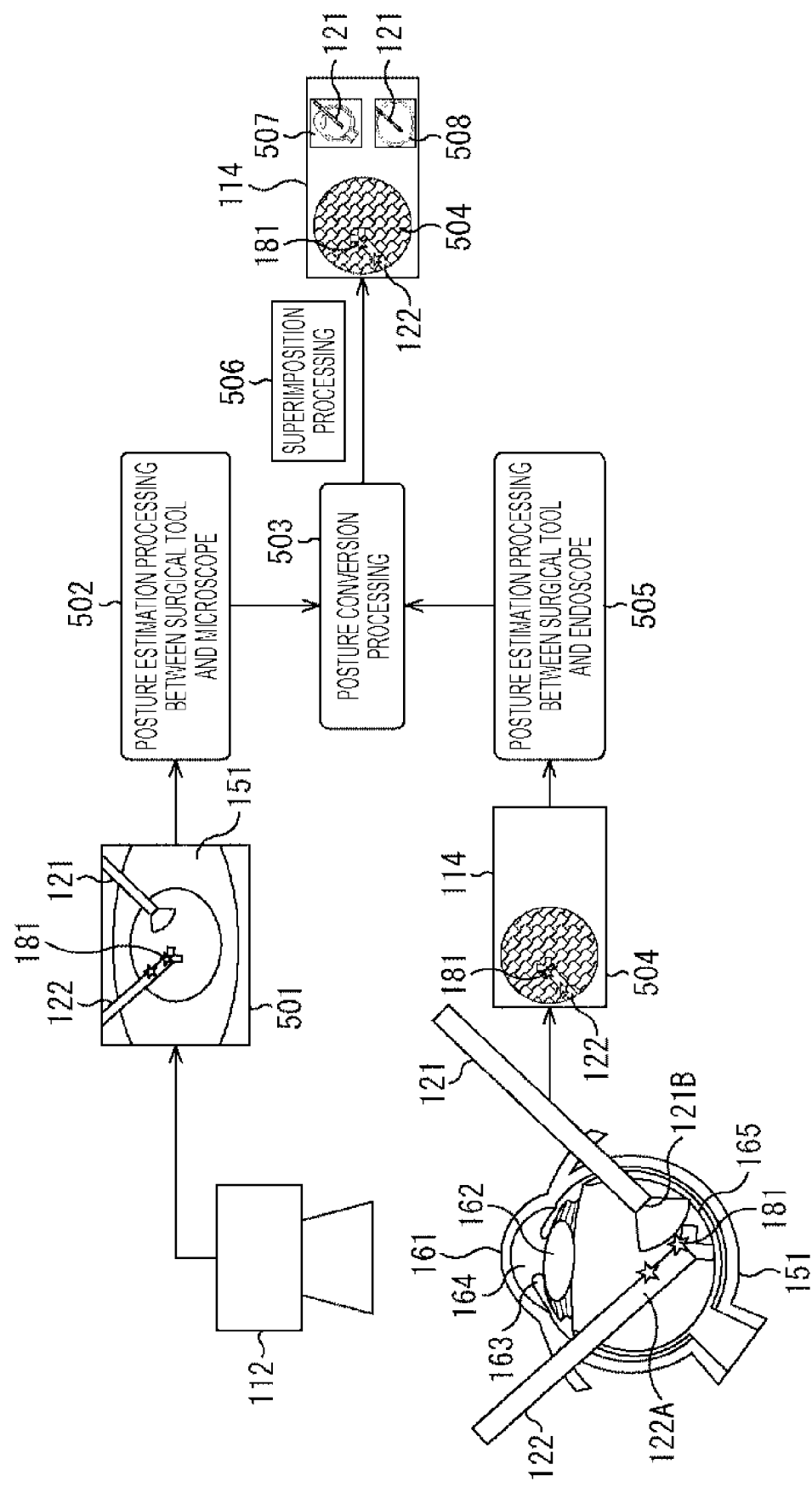
FIG. 8 is a diagram for explaining eye surgery according to an embodiment of the present technology.

FIG. 8 is a diagram for explaining eye surgery according to an embodiment of the present technology. Next, a third embodiment will be described with reference to FIG. 8.

(1) Principle of Posture Estimation

FIG. 8 shows a cross-sectional configuration of the subject eye 151 of the subject person 131, as similar to the case in FIG. 3. An upper part of the subject eye 151 is covered with a cornea 161. A crystalline lens 162 exists further behind an anterior chamber 164 under the cornea 161, and an iris 163 exists on the left and right thereof. Furthermore, a retina 165 exists behind the spherical subject eye 151.

The insertion unit 121A of the intraocular endoscope 121 is inserted to the subject eye 151, and the internal state is photographed. In addition, the insertion unit 122A of the surgical tool 122 is also inserted to the subject eye 151. In the first embodiment, the marker 171 is displayed on the insertion unit 121A of the intraocular endoscope 121. However, in the third embodiment, a marker 181 for confirming the posture of the surgical tool 122 is displayed on the insertion unit 122A of the surgical tool 122. This marker 181 can be confirmed with a microscopic image photographed by the surgical microscope 112 and the endoscopic image photographed by the intraocular endoscope 121.

The marker 181 is similar to the marker 171 already described with reference to FIG. 4, and since description is redundant, description thereof will be omitted.

A microscopic image 501 is obtained by photographing the subject eye 151 with the surgical microscope 112. A marker 181 projected on the microscopic image 501 can be analyzed so that posture estimation processing 502 for estimating the posture of the surgical tool 122 with respect to the surgical microscope 112 can be performed.

Similarly, an endoscopic image 504 is obtained by photographing the subject eye 151 with the intraocular endoscope 121. A marker 181 projected on the endoscopic image 504 can be analyzed so that posture estimation processing 505 for estimating the posture of the surgical tool 122 with respect to the intraocular endoscope 121 can be performed.

Further, a relative posture of the intraocular endoscope 121 with respect to the surgical microscope 112 can be obtained by performing posture conversion processing 503 on the posture of the surgical tool 122 with respect to the surgical microscope 112 and the posture of the surgical tool 122 with respect to the intraocular endoscope 121.

An endoscopic image 504 photographed by the intraocular endoscope 121 and graphic images 507 and 508 representing the posture that has been estimated of the intraocular endoscope 121 are displayed on the presentation unit 114 by performing superimposition processing 506. The details of the graphic images 507 and 508 representing the posture will be described later as posture information. Here, graphic images 507 and 508 representing the posture of the intraocular endoscope 121 are displayed in a graphic of the sectional shape of the subject eye 151.

(2) Functional Block of Surgical System

Figure 9:
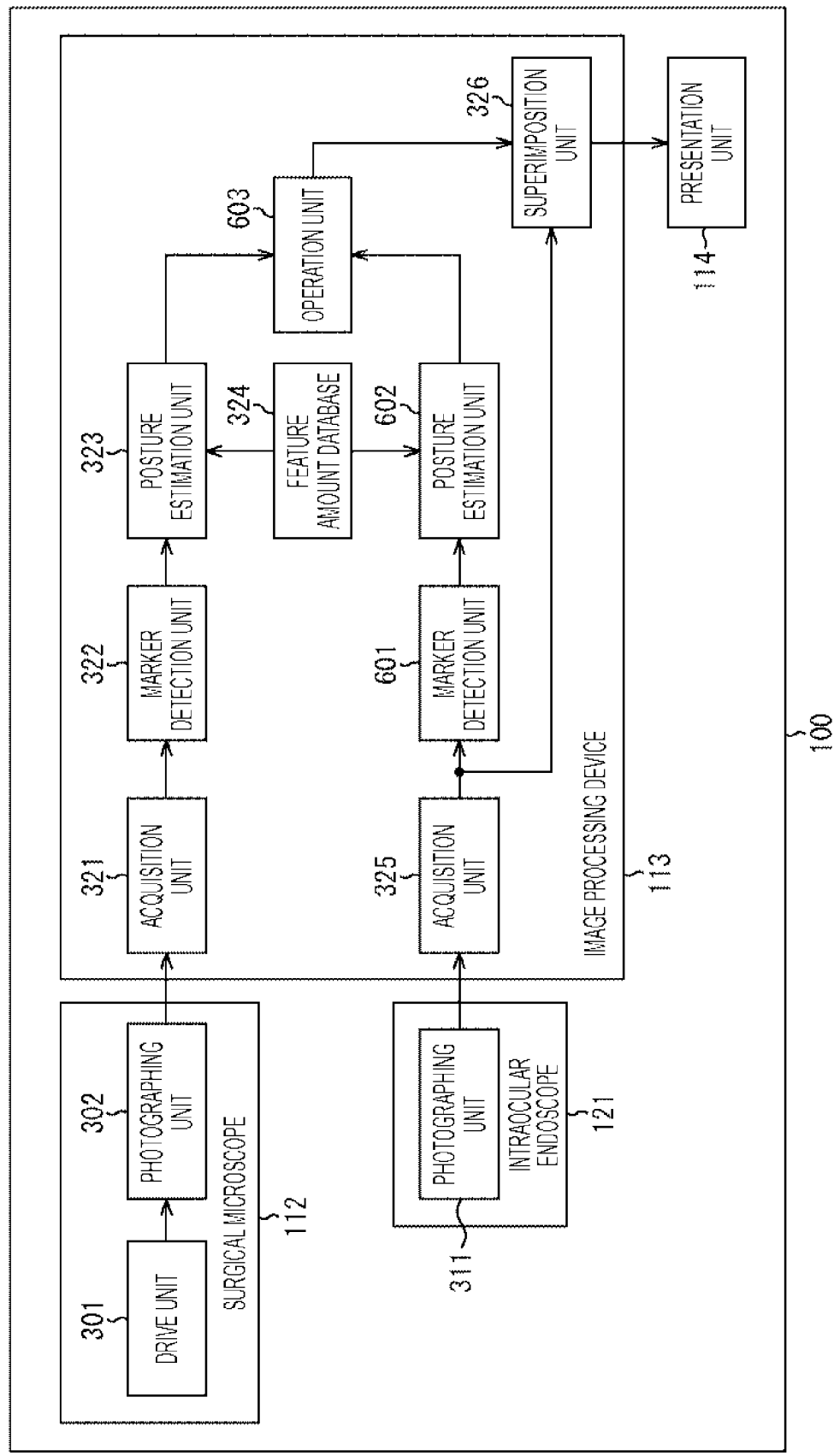
FIG. 9 is a block diagram showing a configuration of a surgical system of the present technology.

FIG. 9 is a block diagram showing a functional configuration of a surgical system of the present technology. As shown in FIG. 9, the surgical microscope 112 has the drive unit 301 and the photographing unit 302, and the intraocular endoscope 121 has the photographing unit 311, as similar to the case of the first embodiment of FIG. 5. Furthermore, it is also similar to the case of the first embodiment that the image processing device 113 has the acquisition unit 321, the marker detection unit 322, the posture estimation unit 323, and the feature amount database 324 that process signals from the imaging unit 302 of the surgical microscope 112. Furthermore, it is also similar to the case of the first embodiment that the image processing device 113 has the acquisition unit 325 that acquires the output of the imaging unit 311 of the intraocular endoscope 121, and the superimposition unit 326 that superimposes the output of the acquisition unit 325 on the posture information.

In the image processing device 113 according to the third embodiment shown in FIG. 9, not only the acquisition unit 321, the marker detection unit 322, and the posture estimation unit 323 as a systems for processing signals from the imaging unit 302 of the surgical microscope 112, but also a system for processing signals from the intraocular endoscope 121 is provided. In other words, an acquisition unit 325, a marker detection unit 601, and a posture estimation unit 602 are provided as systems for processing signals from the imaging unit 311 of the intraocular endoscope 121.

The acquisition unit 325 acquires an image signal of an endoscopic image obtained by photographing by the photographing unit 311 of the intraocular endoscope 121. The marker detection unit 601 detects the marker 181 from the image signal of the endoscopic image acquired by the acquisition unit 325. The posture estimation unit 602 estimates the posture of the surgical tool 122 from the photographing state of the marker 181 detected by the marker detection unit 601.

The feature amount database 324 stores not only the feature amount of the posture of the marker 181 displayed on the insertion unit 122A of the surgical tool 122 with respect to the surgical microscope 112 but also the feature amount of the posture of the marker 181 with respect to the intraocular endoscope 121. Then, as similar to the case where the posture estimation unit 323 detects the posture of the surgical tool 122 with respect to the surgical microscope 112, the posture estimation unit 602 detects the posture of the surgical tool 122 with respect to the intraocular endoscope 121.

Furthermore, the image processing device 113 is provided with an operation unit 603 that performs posture conversion processing 503. From the posture of the surgical tool 122 with respect to the surgical microscope 112 estimated by the posture estimation unit 323 and the posture of the surgical tool 122 with respect to the intraocular endoscope 121 estimated by the posture estimation unit 602, the operation unit 603 operates the posture of the intraocular endoscope 121 with respect to the surgical microscope 112.

The superimposition unit 326 superimposes the image representing the posture of the intraocular endoscope 121 supplied from the operation unit 603 and the endoscopic image of the intraocular endoscope 121 acquired by the acquisition unit 325, and outputs the superimposed image to the presentation unit 114 for presentation.

(3) Image Processing

Figure 10:
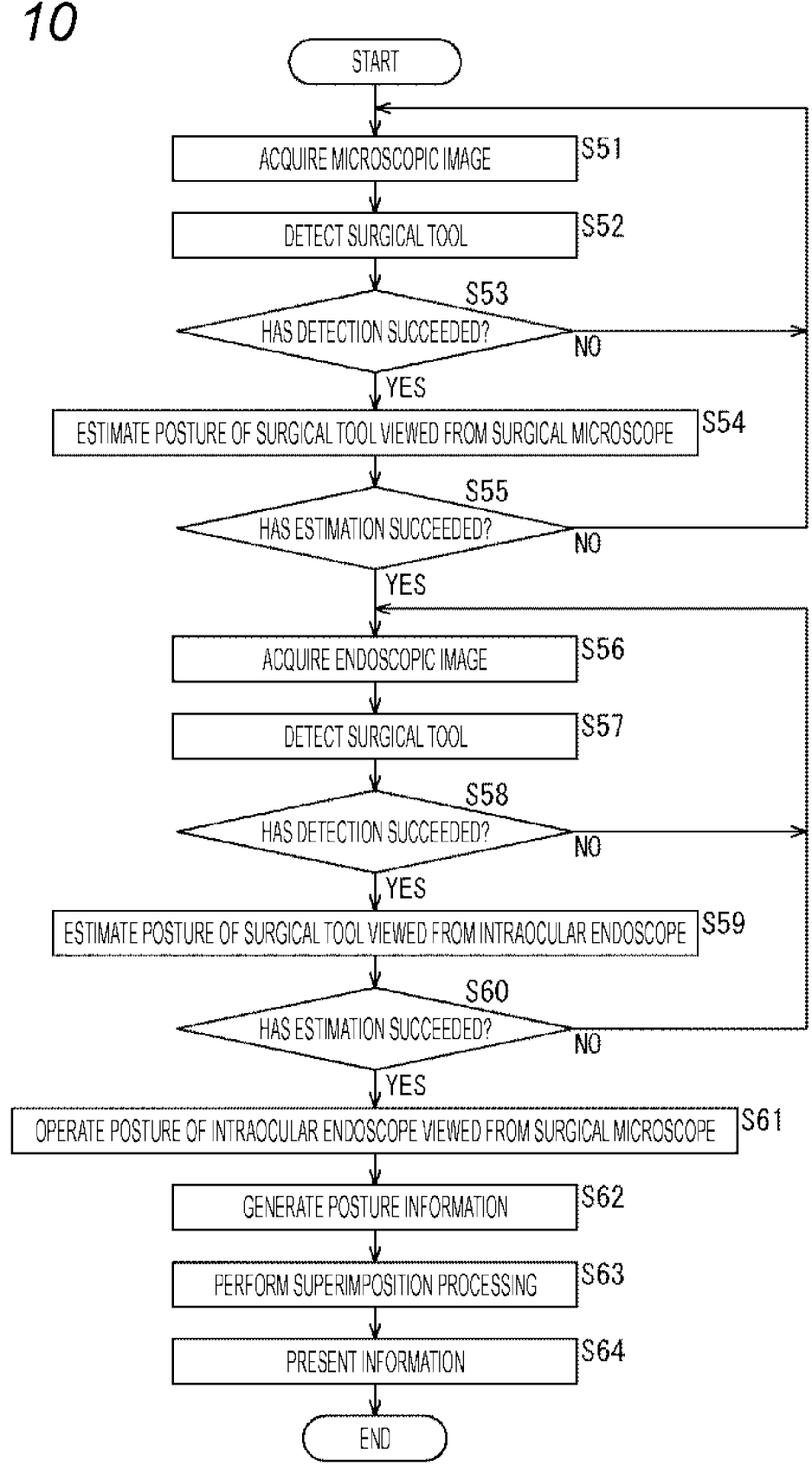
FIG. 10 is a flowchart for explaining image processing of the present technology.

Next, operation of the surgical system 100 of FIG. 9 will be described with reference to FIG. 10. FIG. 10 is a flowchart for explaining image processing of the present technology.

In step S51, the acquisition unit 321 acquires the microscopic image. The image signal of the acquired microscopic image is supplied to the marker detection unit 322. That is, the subject eye 151 is photographed by the imaging unit 302 that has been arranged at a predetermined position in advance by the drive unit 301. As shown in FIG. 8, when the insertion unit 122A of the surgical tool 122 is inserted to the subject eye 151, the marker 181 appears in the acquired microscopic image.

In step S52, the marker detection unit 322 detects the surgical tool 122. In other words, the surgical tool 122 is detected from the acquired microscopic image photographed by the photographing unit 302 of the surgical microscope 112. In step S53, the marker detection unit 322 determines whether detection is successful. In a case where the marker 181 cannot be detected, the processing returns to step S51. That is, the processing of detecting the marker 181 from the acquired image is repeated.

In a case where the detection of the marker 181 succeeds, the marker detection unit 322 supplies the detection result to the posture estimation unit 323. In step S54, the posture estimation unit 323 estimates the posture of the surgical tool 122 as viewed from the surgical microscope 112.

In other words, as described with reference to FIG. 4, the state of the marker 181 in the microscopic image obtained by photographing the surgical tool 122 with the surgical microscope 112 varies depending on the posture of the surgical tool 122. The image of the marker 181 corresponding to an arbitrary rotation angle is stored in the feature amount database 324, and the rotation angle of the surgical tool 122 viewed from the surgical microscope 112 can be estimated by retrieving an image corresponding to the observed image of the marker 181 from the stored image of the marker 181.

The position and orientation can be estimated by solving the PNPP. In other words, the same processing as in step S14 in FIG. 6 is performed.

In step S55, the posture estimation unit 323 determines whether the estimation is successful. In a case where the posture of the surgical tool 122 cannot be estimated yet, the processing returns to step S51, and the processing in step S51 and subsequent steps is repeated.

In a case where the posture of the surgical tool 122 can be estimated, the processing proceeds to step S56.

In step S56, the acquisition unit 325 acquires the endoscopic image. The image signal of the acquired endoscopic image is supplied to the marker detection unit 601. That is, a predetermined portion of the subject eye 151 is photographed by the imaging unit 311 of the intraocular endoscope 121 arranged at a predetermined position by operation by the surgeon 132. As shown in FIG. 8, when the insertion unit 122A of the surgical tool 122 is inserted to the subject eye 151, the marker 181 appears in the acquired endoscopic image.

In step S57, the marker detection unit 601 detects the surgical tool 122. In other words, the surgical tool 122 is detected from the acquired endoscopic image photographed by the photographing unit 311 of the intraocular endoscope 121. In step S58, the marker detection unit 601 determines whether detection is successful. In a case where the marker 181 cannot be detected, the processing returns to step S56. That is, the processing of detecting the marker 181 from the acquired endoscopic image is repeated.

In a case where the detection of the marker 181 succeeds, the marker detection unit 601 supplies the detection result to the posture estimation unit 602. In step S59, the posture estimation unit 602 estimates the posture of the surgical tool 122 as viewed from the intraocular endoscope 121.

In other words, as described with reference to FIG. 4, the state of the marker 181 in the image obtained by photographing the surgical tool 122 with the intraocular endoscope 121 varies depending on the posture of the surgical tool 122. The image of the marker 181 corresponding to an arbitrary rotation angle is stored in the feature amount database 324, and the rotation angle of the surgical tool 122 viewed from the intraocular endoscope 121 can be estimated by retrieving an image corresponding to the observed image of the marker 181 from the stored image of the marker 181.

The position and orientation can be estimated by solving the PNPP. In other words, the same processing as in step S14 in FIG. 6 and step S54 in FIG. 10 is performed.

In step S60, the posture estimation unit 602 determines whether the estimation is successful. In a case where the posture of the surgical tool 122 cannot be estimated yet, the processing returns to step S56, and the processing in step S56 and subsequent steps is repeated.

Note that the processing for the microscopic image of the surgical microscope 112 in steps S51 to S55 and the processing for the endoscopic image of the intraocular endoscope 121 in steps S56 to S60 can be performed in reverse order. Actually, these processes are performed concurrently at the same time.

In a case where the posture of the surgical tool 122 as seen from the intraocular endoscope 121 in step S60 can be estimated, that is, the posture of the surgical tool 122 as viewed from the surgical microscope 112 and the posture of the surgical tool 122 as viewed from the intraocular endoscope 121, the processing of step S61 is performed next. In step S61, the operation unit 603 operates the posture of the intraocular endoscope 121 as viewed from the surgical microscope 112. In other words, the posture of the surgical tool 122 as viewed from the surgical microscope 112 and the posture of the surgical tool 122 as viewed from the intraocular endoscope 121 are converted into the posture of the intraocular endoscope 121 viewed from the surgical microscope 112.

In step S62, the operation unit 603 generates posture information. In other words, posture information corresponding to the operated posture is generated. Details of this posture information will be described later with reference to FIGS. 11 to 14.

In step S63, the superimposition unit 326 performs superimposition processing. In other words, the superimposition unit 326 superimposes the image corresponding to the posture operated by the operation unit 603 on the endoscopic image photographed by the imaging unit 311 of the intraocular endoscope 121 acquired by the acquisition unit 325, and supplies the superimposed image to the presentation unit 114. In step S64, the presentation unit 114 presents information. In other words, an endoscopic image photographed by the intraocular endoscope 121 and an image corresponding to the posture operated by the operation unit 603 are presented on the presentation unit 114.

The surgeon 132 can confirm the posture of the endoscope 121 on the basis of the presented information. Accordingly, the surgeon 132 can perform surgery safely by appropriately applying necessary operations to the intraocular endoscope 121.

Note that since there is a characteristic pattern on the retina 165 itself due to blood vessels, this pattern may be used as a feature point instead of the surgical tool 122.

4. Posture Information

Next, posture information will be described with reference to FIGS. 11 to 14. The surgeon 132 can check the posture of the intraocular endoscope 121 by looking at the posture information and appropriately operate the intraocular endoscope 121. FIGS. 11 to 14 are diagrams showing examples of posture information of the present technology.

Figure 11:
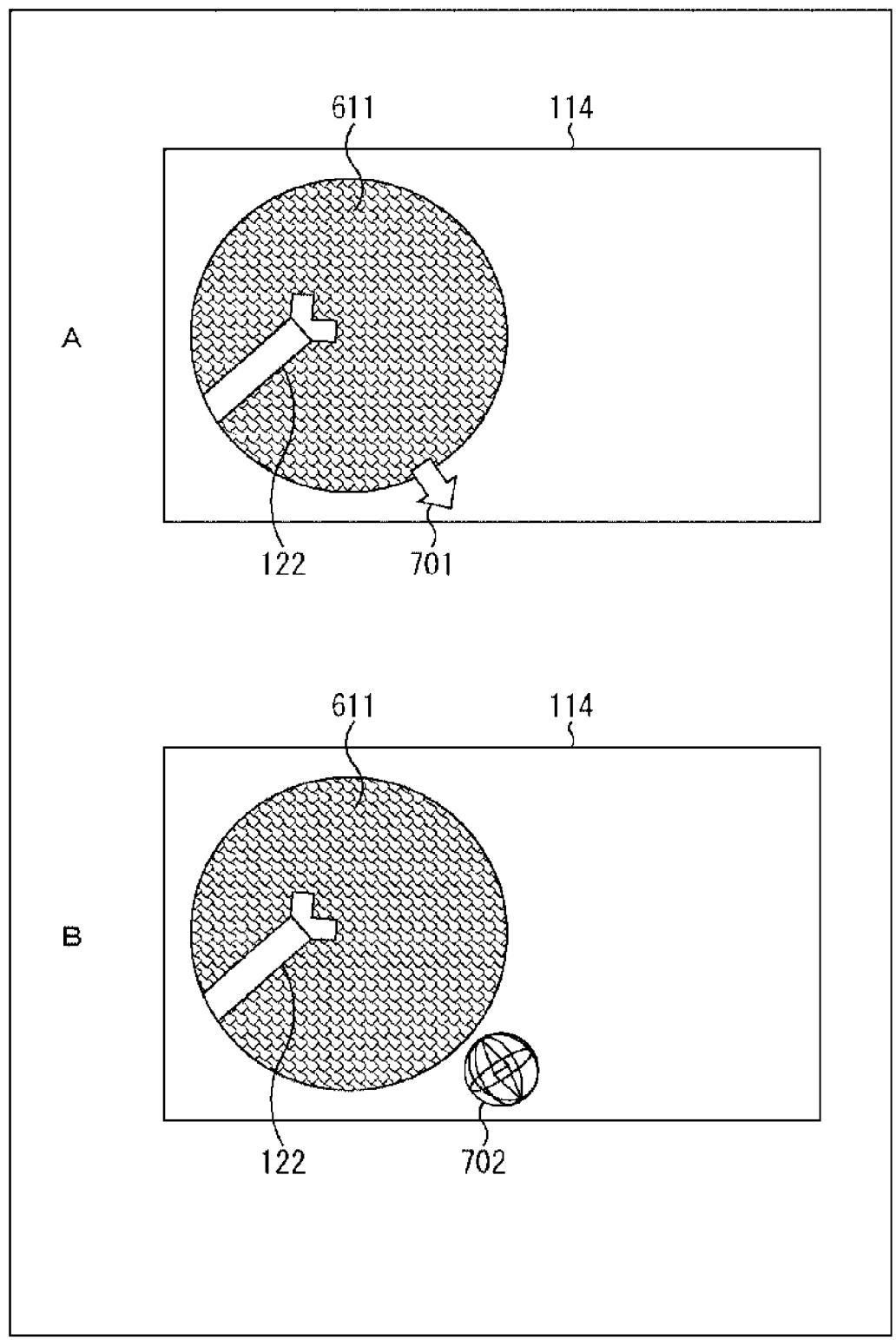
FIG. 11 is a diagram showing an example of posture information of the present technology.

In the example of FIG. 11, a graphic indicating a specific direction is presented as posture information. In A of FIG. 11, an endoscopic image 611 obtained by photographing with the intraocular endoscope 121 is displayed. In the endoscopic image 611, the surgical tool 122 is shown. In the vicinity of the outer peripheral end portion of the endoscopic image 611, a graphic 701 of an arrow is displayed as posture information. The graphic 701 of this arrow indicates the direction of gravity of the intraocular endoscope 121, that is, in this example, if the intraocular endoscope 121 has not rotated, the graphic 701 of the arrow points downward. Accordingly, the surgeon 132 can recognize that the intraocular endoscope 121 is slightly rotated in the clockwise direction from A of FIG. 11.

In the example of B of FIG. 11, an index such as an azimuth magnet indicating the direction of gravity is displayed in a graphic 702 with which a three-dimensional direction is known. With this display, not only a rotation angle (roll angle) in a plane parallel to the display surface of the presentation unit 114 but also a rotation angle (pitch angle) in a plane perpendicular to the display surface of the presentation unit 114 can be recognized.

Note that the specific direction may be the direction specified by the surgeon 132, the direction of the ceiling, the direction of the surgical microscope 112, or the like in addition to the gravity direction.

In a case where only the rotation angle is known, the surgeon 132 can instruct the angle at which the specific direction is located at a predetermined timing, so that the deviation is used as a reference for presentation. Furthermore, in a case where the relative positions and posture of the surgical microscope 112 and the intraocular endoscope 121 are known, the specific direction can be calculated from the position of the surgical microscope 112 as a reference.

Further, the direction in which the surgical tool 122 detected from the microscopic image of the surgical microscope 112 can be presented, or the reference portion such as the fovea of the subject eye 151 can be set as the specific direction. In this case, three-dimensional posture information as shown in B of FIG. 11 can be used.

Figure 12:
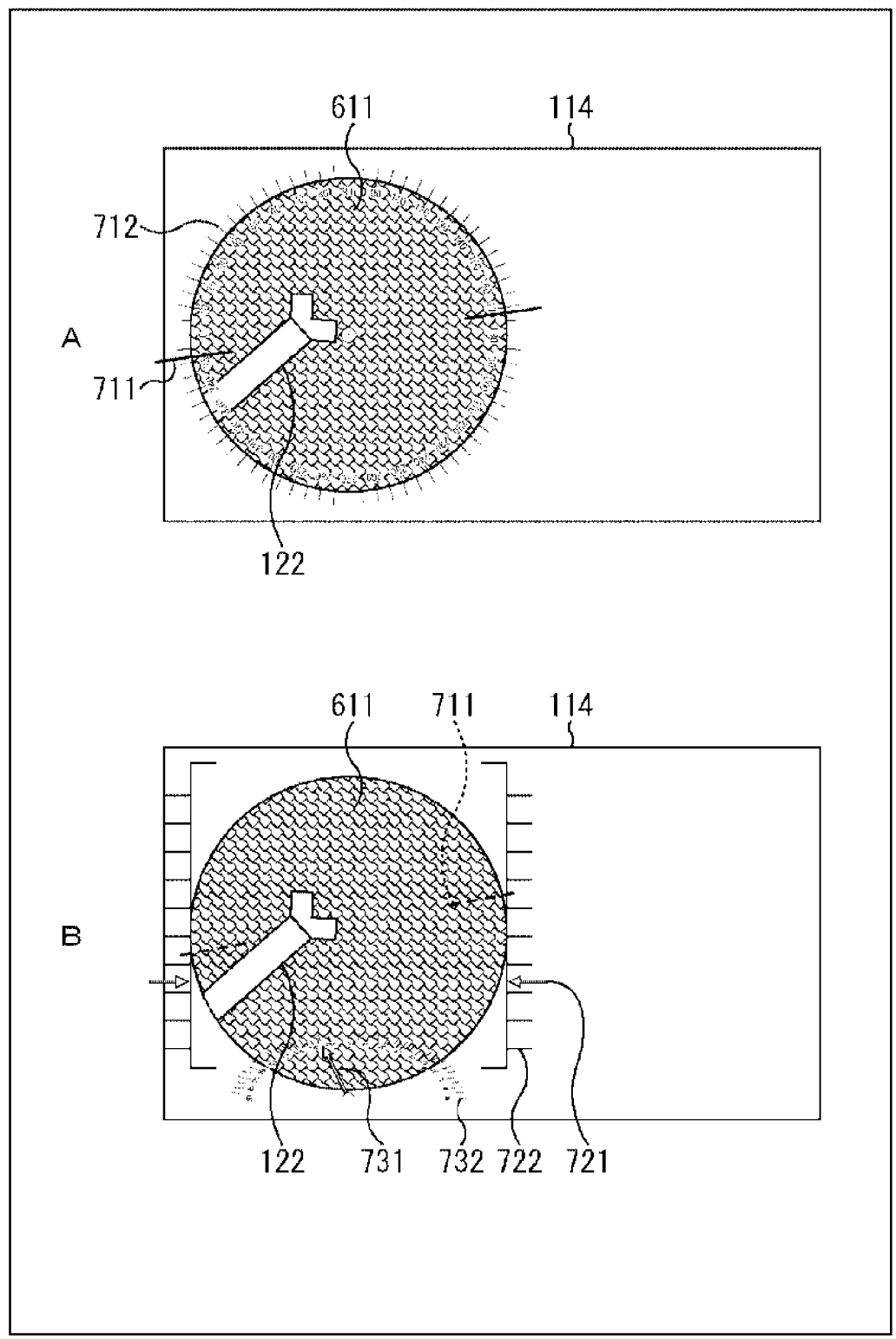
FIG. 12 is a diagram showing an example of posture information of the present technology.

In FIG. 12, the amount of deviation from the specific direction is displayed. In A of FIG. 12, a scale 712 of 0 degrees to 360 degrees roll angle is displayed on the outer peripheral end portion of the endoscopic image 611. Then, a straight line 711 is displayed at an angle position corresponding to the rotation angle of the intraocular endoscope 121. The surgeon 132 can recognize the roll angle of the intraocular endoscope 121 from the angle on the scale indicated by the straight line 711.

In B of FIG. 12, the straight line 711 is displayed so that the roll angle based on the horizontal direction can be seen. However, the roll angle scale (number representing angle) is not displayed. Since the horizontal direction is the reference direction, the roll angle can be recognized intuitively.

A scale 722 representing the distance to the retina is displayed in the up and down direction in the vicinity of the left and right end portions of the endoscopic image 611. A graphic 721 of the arrow is displayed at a position corresponding to the distance between the distal end 121B of the intraocular endoscope 121 and the retina 165. Therefore, the surgeon 132 can read the scale value indicated by the graphic 721 indicated by the arrow to know the position of the intraocular endoscope 121 (in other words, the distance from the tip end 121B to the retina 165), so that the retina 165 is less likely to be damaged.

Further, a scale 732 of an angle based on the head portion 131A of the subject person 131 is displayed below the endoscopic image 611. The graphic 731 of the arrow represents the angle from the reference position (for example, the center line passing through the top portion of the head portion 131A) of the head portion 131A of the intraocular endoscope 121.

Figure 13:
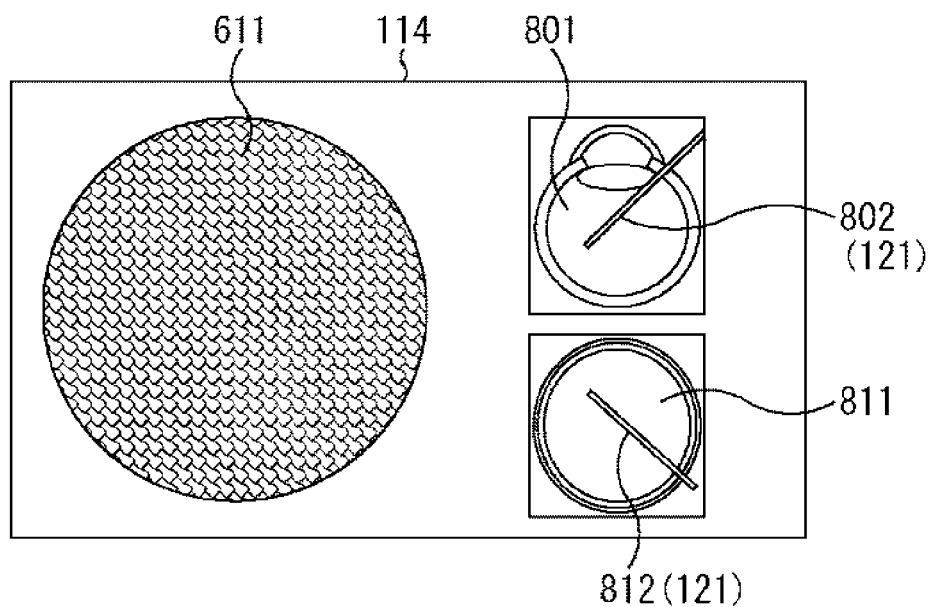
FIG. 13 is a diagram showing an example of posture information of the present technology.
Figure 14:
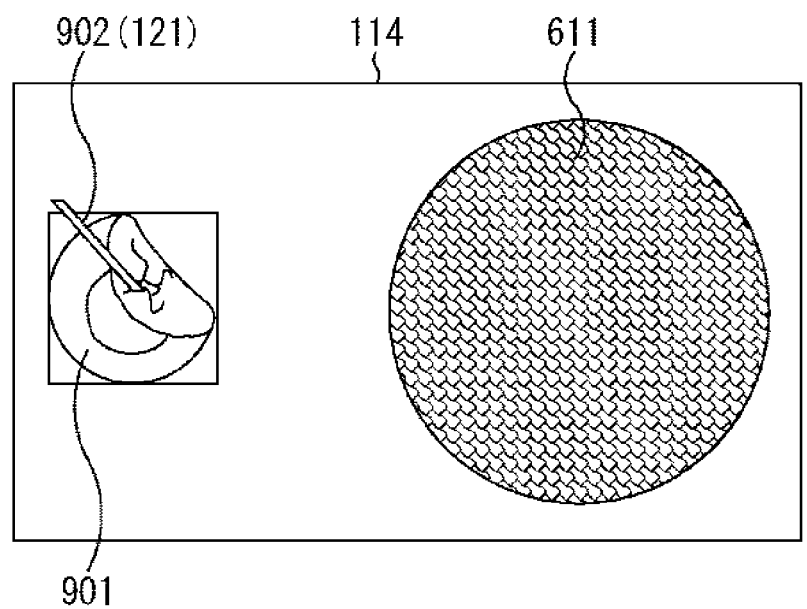
FIG. 14 is a diagram showing an example of posture information of the present technology.

The position and orientation of the intraocular endoscope 121 can also be presented in eyeball model information. FIGS. 13 and 14 show examples of this case. The eyeball model may be created on the basis of an actual three-dimensional image used beforehand for optical coherence tomography (OCT) photographing or the like, or a general eyeball model may be used.

In the example of FIG. 13, information is displayed by a schematic sectional view of the eyeball model. That is, a graphic 801 represents a cross section in a vertical direction of the eyeball model, and a graphic 802 corresponding to the position and orientation of the intraocular endoscope 121 is displayed in the graphic 801. A graphic 811 represents a cross section in a horizontal direction of the eyeball model, and a graphic 812 corresponding to the position and orientation of the intraocular endoscope 121 is displayed in the graphic 811. The surgeon 132 can recognize the position and orientation of the intraocular endoscope 121 from these graphics 801 and 802.

FIG. 14 shows an example of three-dimensional display of posture information based on the eyeball model. In this example, a graphic 902 corresponding to the position and orientation of the intraocular endoscope 121 is displayed on a three-dimensional eyeball model 901. Also in this example, the surgeon 132 can recognize the position and orientation of the intraocular endoscope 121.

As described above, according to the present technology, the orientation of the endoscopic image and the position and posture of the intraocular endoscope 121 can be seen. As a result, operability is improved and safe operation becomes possible. Even beginners can use it easily and learn operations in a short time. In addition, the surgery time is shortened.

It is unnecessary to provide a special sensor, and resistance to distortion of the insertion unit 121A (fiber portion) of the intraocular endoscope 121 is enhanced. In addition, thinning the diameter is not hindered.

Although the embodiments of the present technology have been described above, the present technology is not limited to these embodiments, and various modifications are possible.

<5. Others>

The present technology can also be configured as follows.

(1)

An image processing device including:

an acquisition unit that acquires a microscopic image obtained by photographing a surgical member inserted to a subject with a surgical microscope;

an estimation unit that estimates a relative posture of the surgical member in the subject on the basis of the microscopic image acquired by the acquisition unit; and an output unit that outputs posture information associated with the posture that has been estimated.

(2)

The image processing device described in (1) above, in which the surgical member is an intraocular endoscope.

(3)

The image processing device described in (1) or (2) above, in which the output unit superimposes the posture information on an endoscopic image output by the intraocular endoscope, and outputs the superimposed image.

(4)

The image processing device described in (1), (2) or (3) above, in which the posture includes at least one of a position, an orientation, and a rotation angle.

(5)

The image processing device described in any one of (1) to (4) above, in which the posture information includes a graphic representing a position, an orientation, or a rotation angle on a scale.

(6)

The image processing device described in any one of (1) to (5) above, in which the posture information includes a cross-sectional or three-dimensional view of an eyeball model.

(7)

The image processing device described in any one of (1) to (6) above, in which a marker is displayed on the surgical member, and the estimation unit estimates the relative posture of the surgical member in the subject on the basis of the marker of the microscopic image acquired by the acquisition unit.

(8)

The image processing device described in any one of (1) to (7) above, in which the acquisition unit acquires an image of the intraocular endoscope photographed from an outside of a subject eye as the subject, and the estimation unit estimates the relative posture of the intraocular endoscope in the subject eye on the basis of a feature amount of a portion not inserted to the subject eye of the intraocular endoscope.

(9)

The image processing device described in any one of (1) to (8) above, in which the surgical member is a surgical tool on which a marker is displayed, the acquisition unit acquires the microscopic image of the surgical tool on which the marker is displayed and an endoscopic image of a intraocular endoscope, the estimation unit estimates the relative posture between the surgical tool on which the marker is displayed and the surgical microscope, and also estimates the relative posture between the surgical tool on which the marker is displayed and the intraocular endoscope, and the image processing device further includes an operation unit that operates the relative posture between the surgical microscope and the intraocular endoscope from the relative posture between the surgical tool and the surgical microscope and the relative posture between the surgical tool and the intraocular endoscope.

(10)

An image processing method including:

a step of acquiring a microscopic image obtained by photographing with a surgical microscope a surgical member inserted to a subject and with a marker displayed in an insertion unit;

a step of estimating a relative posture of the surgical member in the subject on the basis of the microscopic image acquired by the acquisition unit; and a step of outputting posture information associated with the posture that has been estimated.

(11)

A surgical system including:

a surgical microscope that photographs a subject; an acquisition unit that acquires a microscopic image obtained by photographing a surgical member inserted to the subject with the surgical microscope;

an estimation unit that estimates a relative posture of the surgical member in the subject on the basis of the microscopic image acquired by the acquisition unit; and an output unit that outputs posture information associated with the posture that has been estimated.

(12)

A surgical member that is inserted to a subject eye of a subject person and is used for surgery of the subject eye, in which a marker that can be observed by a surgical microscope is displayed in an insertion unit to be inserted to the subject eye.

REFERENCE SIGNS LIST

100 Surgical system
111 Surgical table
112 Surgical microscope
113 Image processing device
114 Presentation unit
121 Intraocular endoscope
122 Surgical tool
131 Subject person
131A Head portion

The invention claimed is:

1. An image processing device comprising:
processing circuitry configured to
acquire a microscopic image obtained by photographing an intraocular endoscope inserted into a subject with a surgical microscope;
estimate a relative posture of the intraocular endoscope within the subject by analyzing an image of the intraocular endoscope captured in the microscopic image; and
output posture information regarding the relative posture of the intraocular endoscope by superimposing the posture information onto an endoscopic image obtained by the intraocular endoscope, wherein
the relative posture includes at least one of a position, an orientation, and a rotation angle of the intraocular endoscope within the subject,
the posture information includes a graphic representing the at least one of the position, the orientation, and the rotation angle on a scale, and
the posture information includes a cross-sectional or three-dimensional view of an eyeball model.

2. The image processing device according to claim 1, wherein
a marker is displayed on the intraocular endoscope, and
the processing circuitry estimates the relative posture of the intraocular endoscope in the subject on the basis of the marker in the microscopic image captured by the surgical microscope.

3. The image processing device according to claim 1, wherein
the processing circuitry acquires an image of the intraocular endoscope photographed from an outside of a subject eye as the subject, and
the processing circuitry estimates the relative posture of the intraocular endoscope in the subject eye on the basis of a feature amount of a portion of the intraocular endoscope, the portion not being inserted into the subject eye.

4. An image processing method comprising:
acquiring a microscopic image obtained by photographing an intraocular endoscope inserted into a subject with a surgical microscope;
estimating, using processing circuitry, a relative posture of the intraocular endoscope within the subject by analyzing an image of the intraocular endoscope captured in the microscopic image; and
outputting posture information regarding the relative posture of the intraocular endoscope by superimposing the posture information onto an endoscopic image obtained by the intraocular endoscope, wherein
the relative posture includes at least one of a position, an orientation, and a rotation angle of the intraocular endoscope within the subject,
the posture information includes a graphic representing the at least one of the position, the orientation, and the rotation angle on a scale, and
the posture information includes a cross-sectional or three-dimensional view of an eyeball model.

5. A surgical system comprising:
a surgical microscope that photographs a subject;
an intraocular endoscope configured to be inserted into the subject, and obtain an endoscopic image inside the subject; and
processing circuitry configured to
acquire a microscopic image obtained by photographing the intraocular endoscope inserted into the subject with the surgical microscope;
estimate a relative posture of the intraocular endoscope within the subject by analyzing an image of the intraocular endoscope captured in the microscopic image; and
output posture information regarding the relative posture of the intraocular endoscope by superimposing the posture information onto an endoscopic image obtained by the intraocular endoscope, wherein
the relative posture includes at least one of a position, an orientation, and a rotation angle of the intraocular endoscope within the subject,
the posture information includes a graphic representing the at least one of the position, the orientation, and the rotation angle on a scale, and
the posture information includes a cross-sectional or three-dimensional view of an eyeball mode.

* * * * *